United States Patent
Bastide et al.

(10) Patent No.: US 10,170,113 B2
(45) Date of Patent: Jan. 1, 2019

(54) CONFLICT RESOLUTION ENHANCEMENT SYSTEM

(71) Applicant: INTERNATIONAL BUSINESS MACHINES CORPORATION, Armonk, NY (US)

(72) Inventors: Paul R. Bastide, Boxford, MA (US); Matthew E. Broomhall, Goffstown, NH (US); Robert E. Loredo, North Miami Beach, FL (US); Fang Lu, Billerica, MA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/708,279

(22) Filed: Sep. 19, 2017

(65) Prior Publication Data

US 2018/0211660 A1    Jul. 26, 2018

Related U.S. Application Data

(63) Continuation of application No. 15/414,661, filed on Jan. 25, 2017.

(51) Int. Cl.
*G10L 15/22* (2006.01)
*G10L 15/26* (2006.01)
(Continued)

(52) U.S. Cl.
CPC ............. *G10L 15/22* (2013.01); *A61M 21/02* (2013.01); *G10L 15/26* (2013.01); *G10L 17/005* (2013.01);
(Continued)

(58) Field of Classification Search
CPC ............................ G06Q 10/10; G06Q 10/109
(Continued)

(56) References Cited

U.S. PATENT DOCUMENTS 7,003,462 B2    2/2006   Shambaugh et al.
7,881,934 B2    2/2011   Endo et al.
(Continued)

FOREIGN PATENT DOCUMENTS

WO    2014122416 A1    8/2014

OTHER PUBLICATIONS

IBM: List of IBM Patents or Patent Applications Treated as Related (Appendix P), Oct. 12, 2017, pp. 1-2.
(Continued)

*Primary Examiner* — Paras D Shah
*Assistant Examiner* — Oluwadamilola M Ogunbiyi
(74) *Attorney, Agent, or Firm* — Michael O'Keefe (57) ABSTRACT

A method for controlling a plurality of environmental factors that trigger a negative emotional state is provided. The method may include analyzing a plurality of user data when a user experiences a plurality of various environmental factors. The method may also include determining an emotional state experienced by the user when each of the plurality of various environmental factors is present based on the plurality of user data. The method may include receiving a plurality of calendar information associated with a user account. The method may also include identifying an upcoming event based on the plurality of calendar information. The method may include identifying an environmental factor within the plurality of various environmental factors is present at the upcoming event. The method may also include, in response to determining the environmental factor causes the user to experience a negative emotional state, executing an accommodation method based on the environmental factor.

1 Claim, 5 Drawing Sheets

(51) Int. Cl.
  *G06Q 10/10* (2012.01)
  *G10L 25/63* (2013.01)
  *G10L 17/00* (2013.01)
  *A61M 21/02* (2006.01)
  *A61M 21/00* (2006.01)

(52) U.S. Cl.
  CPC ........ *G10L 25/63* (2013.01); *A61M 2021/005* (2013.01); *A61M 2021/0027* (2013.01); *A61M 2205/3303* (2013.01); *G06Q 10/10* (2013.01); *G06Q 10/109* (2013.01)

(58) Field of Classification Search
  USPC .......................................................... 704/270
  See application file for complete search history.

(56) References Cited

U.S. PATENT DOCUMENTS

| | | | |
|---|---|---|---|
| 9,257,122 B1 | 2/2016 | Cancro et al. | |
| 9,652,113 B1* | 5/2017 | Colson | H04L 12/1822 |
| 2002/0138271 A1* | 9/2002 | Shaw | G06F 17/2765 |
| | | | 704/270 |
| 2009/0192399 A1* | 7/2009 | Choi | A61B 5/02405 |
| | | | 600/519 |
| 2009/0204714 A1* | 8/2009 | Ferrara | G06Q 10/10 |
| | | | 709/228 |
| 2010/0185933 A1* | 7/2010 | Coffman | G06Q 10/10 |
| | | | 715/230 |
| 2011/0125063 A1 | 5/2011 | Shalon et al. | |
| 2011/0142250 A1* | 6/2011 | Schmale | G01R 33/288 |
| | | | 381/73.1 |
| 2011/0295607 A1* | 12/2011 | Krishnan | G10L 17/26 |
| | | | 704/270 |
| 2012/0116186 A1* | 5/2012 | Shrivastav | A61B 5/0507 |
| | | | 600/301 |
| 2012/0128140 A1* | 5/2012 | Geppert | G06F 9/543 |
| | | | 379/93.17 |
| 2012/0197523 A1* | 8/2012 | Kirsch | G01C 21/362 |
| | | | 701/426 |
| 2013/0144619 A1* | 6/2013 | Lord | G06F 3/165 |
| | | | 704/235 |
| 2013/0234826 A1* | 9/2013 | Sekiguchi | H04N 21/42201 |
| | | | 340/5.53 |
| 2014/0112556 A1* | 4/2014 | Kalinli-Akbacak | G10L 25/63 |
| | | | 382/128 |
| 2014/0192141 A1* | 7/2014 | Begeja | H04N 7/147 |
| | | | 348/14.08 |
| 2014/0250174 A1* | 9/2014 | Zamer | H04L 67/22 |
| | | | 709/204 |
| 2014/0350349 A1* | 11/2014 | Geurts | A61B 5/0022 |
| | | | 600/300 |
| 2015/0067044 A1* | 3/2015 | Bakaev | H04L 65/403 |
| | | | 709/204 |
| 2015/0081299 A1* | 3/2015 | Jasinschi | A61B 5/165 |
| | | | 704/246 |
| 2015/0163067 A1* | 6/2015 | Cudak | H04W 4/21 |
| | | | 709/204 |
| 2015/0287403 A1* | 10/2015 | Holzer Zaslansky | G06T 13/205 |
| | | | 704/231 |
| 2016/0372110 A1* | 12/2016 | Waltermann | G10L 15/22 |
| 2017/0011210 A1* | 1/2017 | Cheong | H04W 12/06 |
| 2017/0084295 A1 | 3/2017 | Tsiartas et al. | |
| 2017/0112431 A1* | 4/2017 | Levine | A61B 5/486 |
| 2017/0162187 A1* | 6/2017 | Ohtani | G10L 13/033 |
| 2017/0206913 A1* | 7/2017 | Nahman | G10L 21/007 |
| 2018/0012230 A1* | 1/2018 | Feigenblat | G06Q 50/01 |

OTHER PUBLICATIONS

Lerner, "We built voice modulation to mask gender in technical interviews. Here's what happened," interviewing.io. blog, Jun. 29, 2016, http://blog.interviewing.io/we-built-voice-modulation-to-mask-gender-in-technical-interviews-heres-what-happened/, pp. 1-9.

Mell, et al., "The NIST Definition of Cloud Computing," National Institute of Standards and Technology, U.S. Department of Commerce, Special Publication 800-145, Sep. 2011, pp. 1-7.

Bastide et al., U.S. Appl. No. 15/414,661, filed Jan. 25, 2017, titled "Context-Aware Translation Memory to Facilitate More Accurate Translation", pp. 1-31.

\* cited by examiner

CONFLICT RESOLUTION ENHANCEMENT SYSTEM

BACKGROUND

The present invention relates, generally, to the field of computing, and more particularly to speech recognition systems.

Speech recognition may relate to a computer's ability to identify and respond to human speech. Speech recognition may encompass systems that analyze human speech to identify specific commands, such as voice dialing, call routing, data entry, and speech-to-text. Frequently, a training phase is implemented by speech recognition software to improve the identification of spoken words. Furthermore, speech recognition may also include speaker identification where the system may be capable of identifying a speaker rather than the words being spoken based on the specific person's voice patterns.

SUMMARY

Embodiments of the present invention disclose a method, computer system, and a computer program product for controlling a plurality of environmental factors that trigger a negative emotional state. The present invention may include analyzing a plurality of user data when a user experiences a plurality of various environmental factors. The present invention may also include determining an emotional state experienced by the user when each of the plurality of various environmental factors is present based on the plurality of analyzed user data. The present invention may further include receiving a plurality of calendar information associated with a user account. The present invention may also include identifying an upcoming event based on the plurality of received calendar information. The present invention may further include identifying an environmental factor within the plurality of various environmental factors is present at the identified upcoming event. The present invention may also include, in response to determining the identified environmental factor causes the user to experience a negative emotional state, executing an accommodation method based on the identified environmental factor.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques may be omitted to avoid unnecessarily obscuring the presented embodiments.

Embodiments of the present invention relate to the field of computing, and more particularly to speech recognition. The following described exemplary embodiments provide a system, method, and program product to, among other things, analyze an individual's experience with various sound and voice types to identify specific instances to which the individual may be sensitive and perform an assistance method to correct the sensitive situation for the individual. Therefore, the present embodiment has the capacity to improve the technical field of speech recognition by improving a user's productivity when the user has specific sensitivities that may require visual and/or audio assistance or modification.

As previously described, speech recognition may relate to a computer's ability to identify and respond to human speech. Speech recognition may encompass systems that analyze human speech to identify specific commands, such as voice dialing, call routing, data entry, and speech-to-text. Frequently, a training phase is implemented by speech recognition software to improve the identification of spoken words. Furthermore, speech recognition may also include speaker identification where the system may be capable of identifying a speaker rather than the words being spoken based on the specific person's voice patterns.

Some individuals may experience sensitivities to various types of sound or visuals, such as an individual diagnosed with autism spectrum disorder being sensitive to loud voices or bright lights. Furthermore, an individual may be sensitive to a particular vocal type due to a past negative experience. For example, a person may have experienced a traumatic event with a distinctively voiced individual and may now experience a sensitivity when other individuals with similar voices are heard. Sensitivities to various sounds and voices may affect an individual's productivity. For example, if a person experiences a voice sensitivity during a meeting, that person may be unable to effectively listen or communicate due to the unpleasant voice or sound being heard. In similar situations, a presenter may not be able to identify when a particular meeting attendee or presentation listener is sensitive to a sound or voice. Since the presentation method is not altered to accommodate all individuals, the presenter may not be able to effectively convey the presentation message to all meeting attendees or presentation listeners. As such, it may be advantageous to, among other things, identify individuals with specific sensitivities and provide an accommodation to the identified individuals.

According to one embodiment, a user's experience with various environments, such as sounds, voices, and lighting situations, may be observed and analyzed to establish a corresponding data model that may link the user's emotional state with the various environments. The system may then determine if the user is likely to experience any of the various environments that the corresponding data model links with a negative emotional state based on the user's upcoming calendar events. If the user is likely to experience a negative emotional state, the system may identify an appropriate accommodation to assist the user is either reducing or eliminating the negative emotional state. For example, if the user is sensitive to a particular web presenter's voice type, the system may mock the presenter's voice with a different person's voice that is more pleasant to the user or a message may be presented that is designed to calm the user. In another embodiment, the presenter may be sent a recommendation to adjust the tone of voice used when presenting in order to deliver or convey the message in a specific manner that allows all attendees or listeners to fully comprehend, including the user.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method, and program product to analyze a user's experiences with various environmental factors and provide an accommodation to the user based on negative user experiences with the detected environmental factors.

Figure 1:
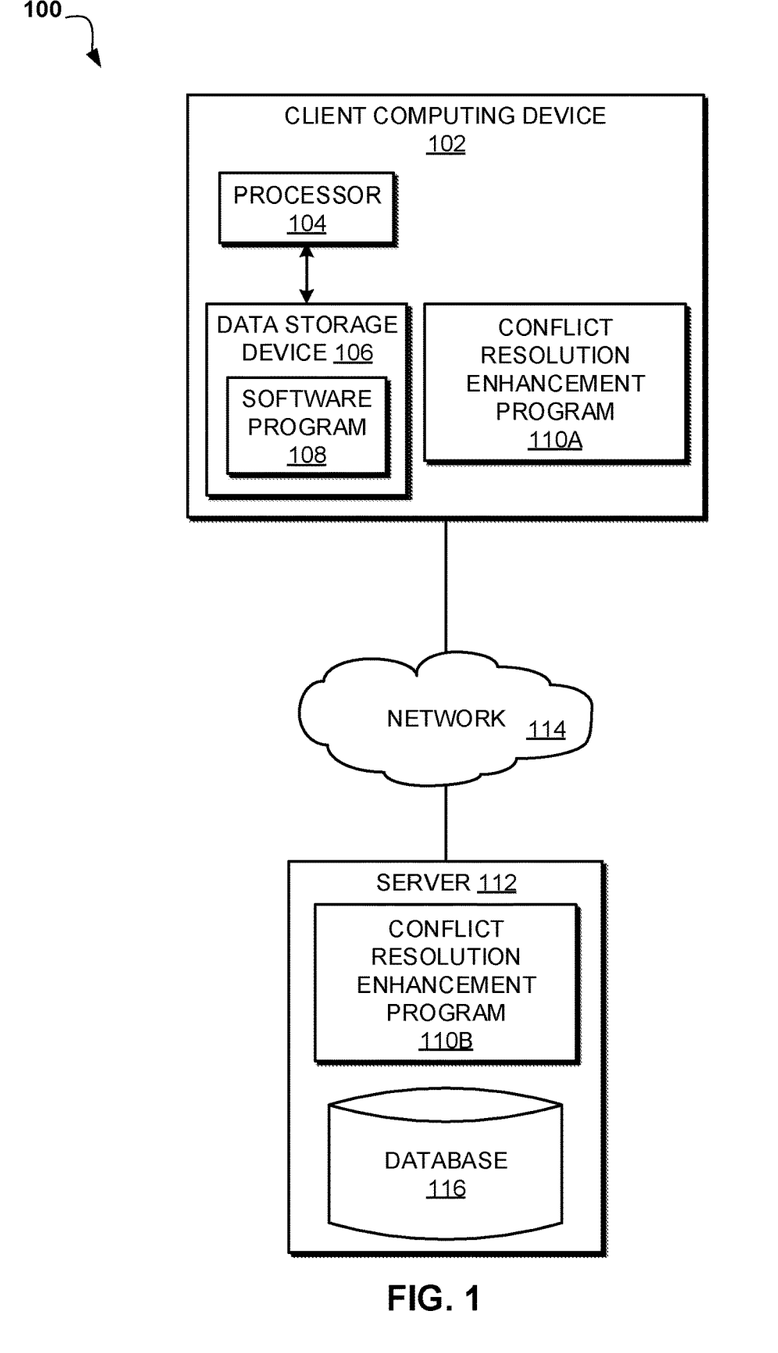
FIG. 1 illustrates an exemplary networked computer environment according to at least one embodiment.

Referring to FIG. 1, an exemplary networked computer environment 100 is depicted, according to at least one embodiment. The networked computer environment 100 may include client computing device 102 and a server 112 interconnected via a communication network 114. According to at least one implementation, the networked computer environment 100 may include a plurality of client computing devices 102 and servers 112, of which only one of each is shown for illustrative brevity.

The communication network 114 may include various types of communication networks, such as a wide area network (WAN), local area network (LAN), a telecommunication network, a wireless network, a public switched network and/or a satellite network. The communication network 114 may include connections, such as wire, wireless communication links, or fiber optic cables. It may be appreciated that FIG. 1 provides only an illustration of one implementation and does not imply any limitations with regard to the environments in which different embodiments may be implemented. Many modifications to the depicted environments may be made based on design and implementation requirements.

Client computing device 102 may include a processor 104 and a data storage device 106 that is enabled to host and run a software program 108 and a conflict resolution enhancement program 110A and communicate with the server 112 via the communication network 114, in accordance with one embodiment of the invention. Client computing device 102 may be, for example, a mobile device, a telephone, a personal digital assistant, a netbook, a laptop computer, a tablet computer, a desktop computer, or any type of computing device capable of running a program and accessing a network. As will be discussed with reference to FIG. 3, the client computing device 102 may include internal components 302a and external components 304a, respectively.

The server computer 112 may be a laptop computer, netbook computer, personal computer (PC), a desktop computer, or any programmable electronic device or any network of programmable electronic devices capable of hosting and running a conflict resolution enhancement program 110B and a database 116 and communicating with the client computing device 102 via the communication network 114, in accordance with embodiments of the invention. As will be discussed with reference to FIG. 3, the server computer 112 may include internal components 302b and external components 304b, respectively. The server 112 may also operate in a cloud computing service model, such as Software as a Service (SaaS), Platform as a Service (PaaS), or Infrastructure as a Service (IaaS). The server 112 may also be located in a cloud computing deployment model, such as a private cloud, community cloud, public cloud, or hybrid cloud.

According to the present embodiment, the conflict resolution enhancement program 110A, 110B may be a program capable of analyzing user experiences with various environmental factors, such as sound and lighting, and creating a data model that identifies the specific environmental factors with which the user experiences sensitivities or negative emotional states. Upon identifying that an upcoming event may trigger a sensitivity or negative emotional state in the user, the conflict resolution enhancement program 110A, 110B may provide accommodations to the user or suggest a third party, such as a meeting presenter, alter specific attributes, such as voice level, to allow the user to avoid the sensitivity or negative emotional state. The conflict resolution enhancement method is explained in further detail below with respect to FIG. 2.

Figure 2:
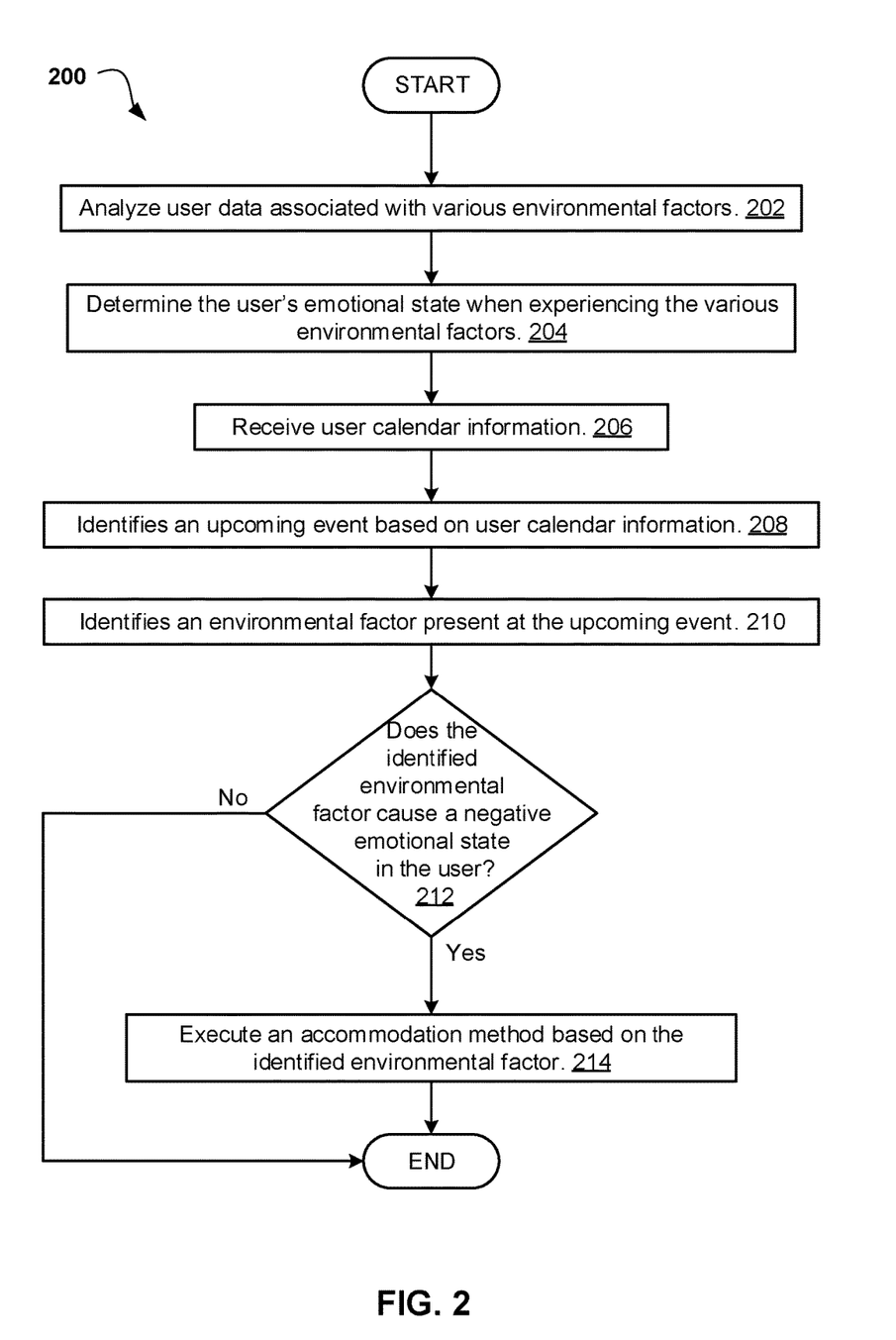
FIG. 2 is an operational flowchart illustrating a conflict resolution enhancement process according to at least one embodiment.

Referring now to FIG. 2, an operational flowchart illustrating a conflict resolution enhancement process 200 is depicted, according to at least one embodiment. At 202, the conflict resolution enhancement program 110A, 110B analyzes user data, such as user vital sign data, associated with various environmental factors. The conflict resolution enhancement program 110A, 110B may analyze the vital signs experienced by the user when specific environmental factors are present to identify which environmental factors cause the user to experience specific emotions or sensitivities. The vital sign data analyzed by the conflict resolution enhancement program 110A, 110B may include user heart rate, perspiration rate, respiration rate, blood pressure, and body temperature. The various environmental factors may include user location, time of day, ambient noise, ambient lighting, individuals present, speaker identity, speaker voice tone, speaker voice volume, and speaker voice pitch. In at least one embodiment, the user data may include social media data related to user emotions posted on social media networks. For example, the conflict resolution enhancement program 110A, 110B may use known image recognition technology to analyze images and videos posted on a user's social media account to identify environmental factors present and user facial expressions or vocal characteristics to determine the user's reaction to the identified environmental factors.

Next, at 204, the conflict resolution enhancement program 110A, 110B determines the user's emotional state when experiencing the various environmental factors based on the analyzed user data. The conflict resolution enhancement program 110A, 110B may create a data model that stores the user's emotional feedback towards each environmental factor in a data repository, such as database 116. For example, once the conflict resolution enhancement program 110A, 110B has analyzed the user's response to a particular voice, the conflict resolution enhancement program 110A, 110B may determine the user is stressed when hearing the voice based on the user's heart rate, respiration rate, and perspiration rate increasing. The conflict resolution enhancement program 110A, 110B may categorize the user's determined emotional state within the created data model. For example, each environmental factor with which the user becomes sad when experiencing may be categorized together in the created data model.

Next, at 206, the conflict resolution enhancement program 110A, 110B receives user calendar information. The calendar information may include information related to upcoming events, such as event name, event type, presenter or speaker information, and event date and time. The conflict resolution enhancement program 110A, 110B may receive the calendar information from one or more linked user accounts, such as an email account, a social media account, or an instant messenger account.

Then, at 208, the conflict resolution enhancement program 110A, 110B identifies an upcoming event based on the user calendar information. The conflict resolution enhancement program 110A, 110B may analyze the received calendar information to determine when an event is upcoming based on the event date and time as detailed within the user calendar information. For example, the conflict resolution enhancement program 110A, 110B may analyze the received user calendar information to identify that an event will with occur within one week.

Next, at 210, the conflict resolution enhancement program 110A, 110B identifies an environmental factor present at the identified upcoming event. Using the received user calendar information and other searchable databases (e.g., internet search engines), the conflict resolution enhancement program 110A, 110B may identify an environmental factor present at the identified upcoming event. For example, the conflict resolution enhancement program 110A, 110B may identify the upcoming event will take place at a public park in Phoenix, Ariz., USA based on the received user calendar information. Using an internet search engine, the conflict resolution enhancement program 110A, 110B may determine the date on which the upcoming event takes place will be mostly sunny. Therefore, the conflict resolution enhancement program 110A, 110B may identify a bright light source as an environmental factor present at the identified upcoming event.

Then, at 212, the conflict resolution enhancement program 110A, 110B determines if the identified environmental factor causes the user to experience a negative emotional state. The conflict resolution enhancement program 110A, 110B may be capable of determining if the identified environmental factor may produce a negative emotional state in the user by parsing through the created data model for each negative emotional state (e.g., sadness or stressed) to determine if the identified environmental factor is listed as causing a negative emotional state in the user. For example, in the previous example, the conflict resolution enhancement program 110A, 110B may parse through the created data model to determine whether a bright light source causes the user to experience a negative emotional state. According to one implementation, the method may continue along the operational flowchart 200, if an environmental factor is present that causes the user to experience a negative emotional state. If the conflict resolution enhancement program 110A, 110B determines an environmental factor that causes the user to experience a negative emotional state is present (step 212, "YES" branch), the conflict resolution enhancement program 110A, 110B may continue to step 214 to execute an accommodation method based on the determined environmental factor. If the conflict resolution enhancement program 110A, 110B determines an environmental factor that causes the user to experience a negative emotional state is not present (step 212, "NO" branch), the conflict resolution enhancement program 110A, 110B may terminate.

Next, at 214, the conflict resolution enhancement program 110A, 110B executes an accommodation method based on the identified environmental factor. Once the conflict resolution enhancement program 110A, 110B determines the identified environmental factor may cause the user to experience a negative emotional state, the conflict resolution enhancement program 110A, 110B may execute one or more accommodation methods to aid the user in reducing or eliminating the occurrence of the negative emotional state. The accommodation method taken by the conflict resolution enhancement program 110A, 110B may include visual assistance to the user, audio assistance to the user, or notification to a presenter.

Visual assistance to the user may relate to the conflict resolution enhancement program 110A, 110B presenting a notification on a user device, such as client computing device 102, shortly before the user begins participation or attendance at the upcoming event that is intended to prepare the user for the anticipated environmental factor. For example, if the user is about to join a web conference where the presenter speaks loudly and loud voices are stressful to the user, the conflict resolution enhancement program 110A, 110B may notify the user of the speaker's loud voice before the user joins the web conference and advise the user to lower the device's volume level. In at least one embodiment, the conflict resolution enhancement program 110A, 110B may present an image or video intended to improve the user's emotional state before the user experiences the identified environmental factor that may cause the user to experience a negative emotional state. For example, the conflict resolution enhancement program 110A, 110B may display an image of the user's favorite hobby or a video clip of the user's favorite movie when notifying the user of the identified environmental factor.

Providing audio assistance to the user may relate to the conflict resolution enhancement program 110A, 110B overlaying a sound that causes a negative emotional state in the user with a sound that does not cause a negative emotional state in the user. For example, if loud voices cause a negative emotional state in the user, the conflict resolution enhancement program 110A, 110B may overlay a web conference presenter's loud voice with a softer voice that may not cause a negative emotional state in the user. In a similar example, if a user is attending an in-person conference, the user may wear a hearing device, such as headphones connected to a smartphone, to overlay the presenter's loud voice with a softer voice that may not cause a negative emotional state in the user.

The conflict resolution enhancement program 110A, 110B may also provide a notification to a presenter or speaker that the user is listening to or viewing the presentation but may experience a negative emotional state based on the identified environmental factor. Such a notification may allow the presenter or speaker to alter the identified environmental factor to reduce or eliminate the negative emotional state for the user. For example, if a presentation attendee is sensitive to flashing lights due to autism spectrum disorder, the presenter may remove or limit flashing overhead lights during a multimedia presentation to accommodate the attendee. The conflict resolution enhancement program 110A, 110B may determine the user is attending or participating in the presentation based on the user's acceptance of a meeting invitation or registration for the meeting. Once the conflict resolution enhancement program 110A, 110B determines the user is attending or participating in the presentation, the conflict resolution enhancement program 110A, 110B may transmit the notification to a user device, such as client computing device 102, associated with the speaker or presenter.

It may be appreciated that FIG. 2 provides only an illustration of one implementation and does not imply any limitations with regard to how different embodiments may be implemented. Many modifications to the depicted environments may be made based on design and implementation requirements.

Figure 3:
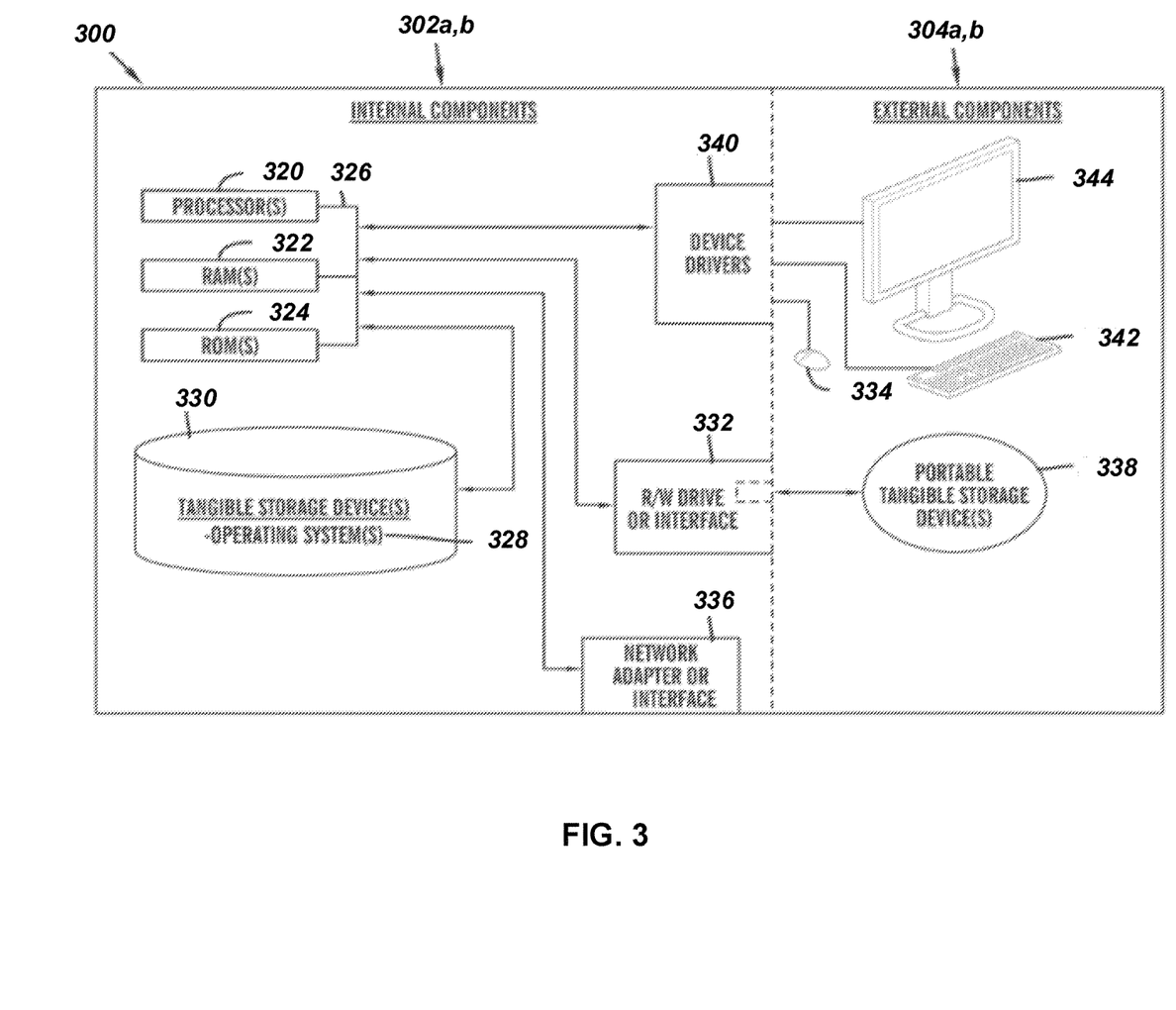
FIG. 3 is a block diagram of internal and external components of computers and servers depicted in FIG. 1 according to at least one embodiment.

FIG. 3 is a block diagram 300 of internal and external components of the client computing device 102 and the server 112 depicted in FIG. 1 in accordance with an embodiment of the present invention. It should be appreciated that FIG. 3 provides only an illustration of one implementation and does not imply any limitations with regard to the environments in which different embodiments may be implemented. Many modifications to the depicted environments may be made based on design and implementation requirements.

The data processing system 302, 304 is representative of any electronic device capable of executing machine-readable program instructions. The data processing system 302, 304 may be representative of a smart phone, a computer system, PDA, or other electronic devices. Examples of computing systems, environments, and/or configurations that may represented by the data processing system 302, 304 include, but are not limited to, personal computer systems, server computer systems, thin clients, thick clients, handheld or laptop devices, multiprocessor systems, microprocessor-based systems, network PCs, minicomputer systems, and distributed cloud computing environments that include any of the above systems or devices.

The client computing device 102 and the server 112 may include respective sets of internal components 302 a,b and external components 304 a,b illustrated in FIG. 3. Each of the sets of internal components 302 include one or more processors 320, one or more computer-readable RAMs 322, and one or more computer-readable ROMs 324 on one or more buses 326, and one or more operating systems 328 and one or more computer-readable tangible storage devices 330. The one or more operating systems 328, the software program 108 and the conflict resolution enhancement program 110A in the client computing device 102 and the conflict resolution enhancement program 110B in the server 112 are stored on one or more of the respective computer-readable tangible storage devices 330 for execution by one or more of the respective processors 320 via one or more of the respective RAMs 322 (which typically include cache memory). In the embodiment illustrated in FIG. 3, each of the computer-readable tangible storage devices 330 is a magnetic disk storage device of an internal hard drive. Alternatively, each of the computer-readable tangible storage devices 330 is a semiconductor storage device such as ROM 324, EPROM, flash memory or any other computer-readable tangible storage device that can store a computer program and digital information.

Each set of internal components 302 a,b also includes a R/W drive or interface 332 to read from and write to one or more portable computer-readable tangible storage devices 338 such as a CD-ROM, DVD, memory stick, magnetic tape, magnetic disk, optical disk or semiconductor storage device. A software program, such as the conflict resolution enhancement program 110A, 110B, can be stored on one or more of the respective portable computer-readable tangible storage devices 338, read via the respective R/W drive or interface 332, and loaded into the respective hard drive 330.

Each set of internal components 302 a,b also includes network adapters or interfaces 336 such as a TCP/IP adapter cards, wireless Wi-Fi interface cards, or 3G or 4G wireless interface cards or other wired or wireless communication links. The software program 108 and the conflict resolution enhancement program 110A in the client computing device 102 and the conflict resolution enhancement program 110B in the server 112 can be downloaded to the client computing device 102 and the server 112 from an external computer via a network (for example, the Internet, a local area network or other, wide area network) and respective network adapters or interfaces 336. From the network adapters or interfaces 336, the software program 108 and the conflict resolution enhancement program 110A in the client computing device 102 and the conflict resolution enhancement program 110B in the server 112 are loaded into the respective hard drive 330. The network may comprise copper wires, optical fibers, wireless transmission, routers, firewalls, switches, gateway computers and/or edge servers.

Each of the sets of external components 304 a,b can include a computer display monitor 344, a keyboard 342, and a computer mouse 334. External components 304 a,b can also include touch screens, virtual keyboards, touch pads, pointing devices, and other human interface devices. Each of the sets of internal components 302 a,b also includes device drivers 340 to interface to computer display monitor 344, keyboard 342, and computer mouse 334. The device drivers 340, R/W drive or interface 332, and network adapter or interface 336 comprise hardware and software (stored in storage device 330 and/or ROM 324).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
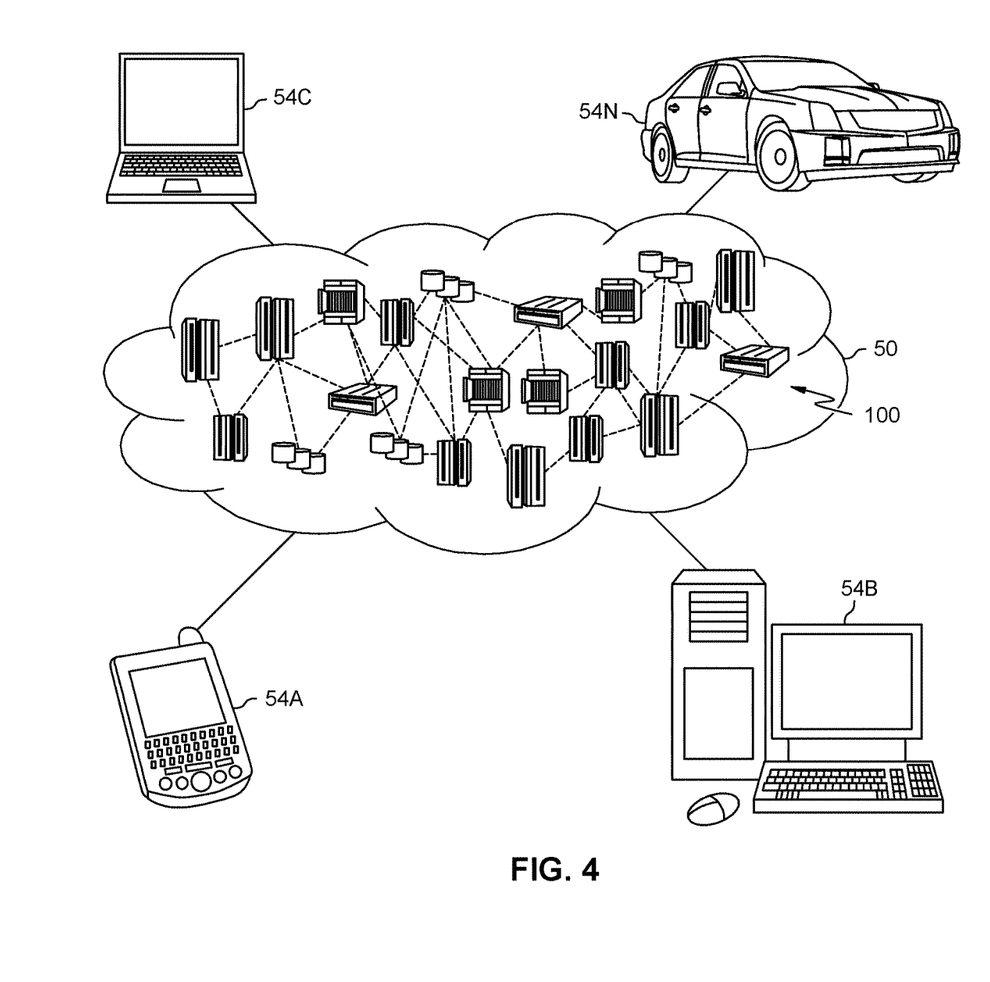
FIG. 4 depicts a cloud computing environment according to an embodiment of the present invention.

Referring now to FIG. 4, illustrative cloud computing environment 50 is depicted. As shown, cloud computing environment 50 comprises one or more cloud computing nodes 100 with which local computing devices used by cloud consumers, such as, for example, personal digital assistant (PDA) or cellular telephone 54A, desktop computer 54B, laptop computer 54C, and/or automobile computer system 54N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 100 and cloud computing environment 50 can communicate with any type of computerized device over any type of network and/or network addressable connection (e.g., using a web browser).

Figure 5:
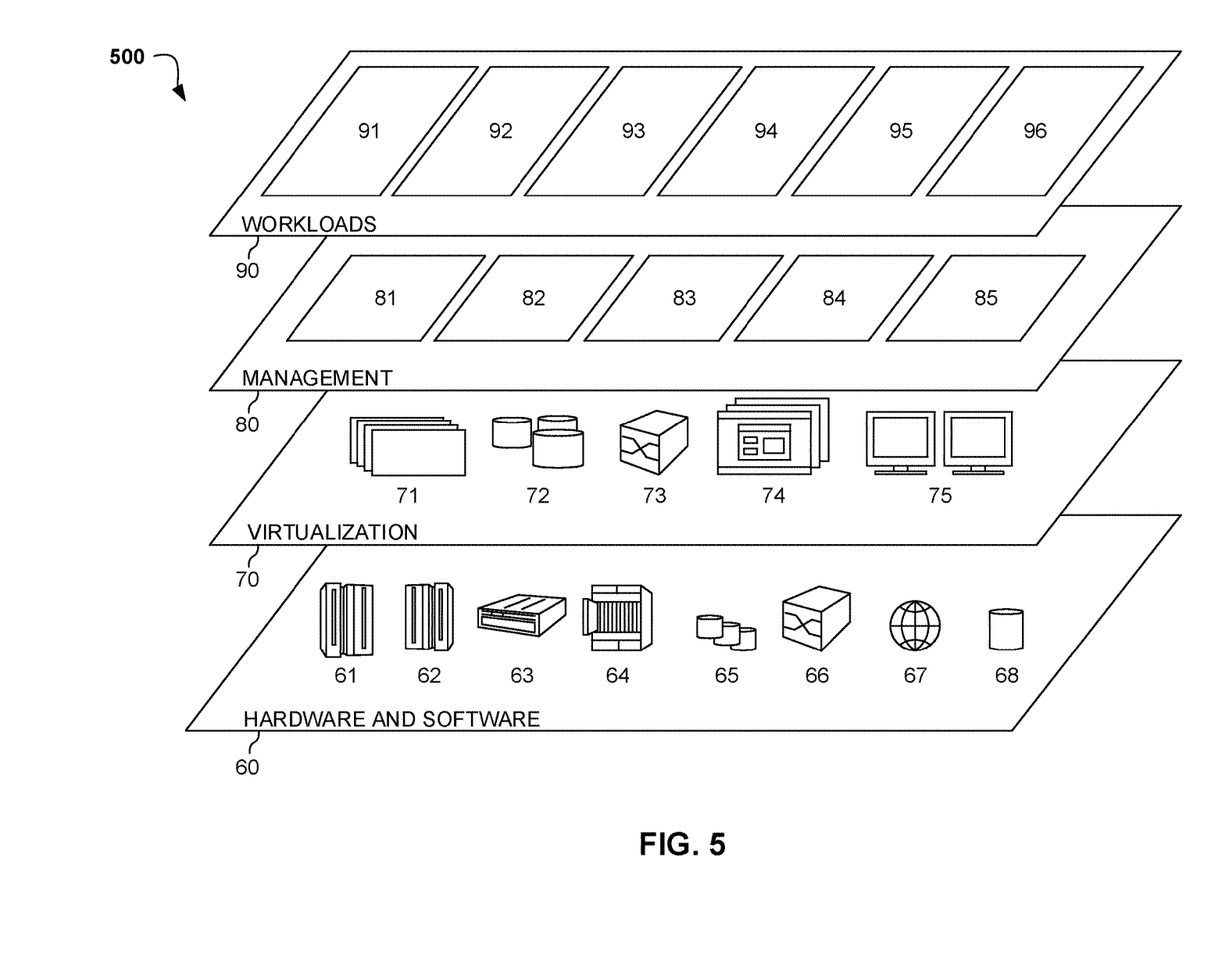
FIG. 5 depicts abstraction model layers according to an embodiment of the present invention.

Referring now to FIG. 5, a set of functional abstraction layers 500 provided by cloud computing environment 50 is shown. It should be understood in advance that the components, layers, and functions shown in FIG. 4 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and conflict resolution enhancement 96. Conflict resolution enhancement 96 may relate to analyzing vital sign data to create a data model that identifies environmental factors to which a user may be sensitive or which create a negative emotion for the user. Furthermore, conflict resolution enhancement 96 may identify upcoming events on a user calendar at which the user may experience a sensitivity or negative emotion and provide an appropriate accommodation.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A processor-implemented method for controlling a plurality of environmental factors that trigger a negative emotional state, the method comprising:

analyzing, by a processor, a plurality of user data when a user experiences a plurality of presenter attributes, wherein the plurality of user data is a plurality of user vital sign data and a plurality of user social media data, and wherein the plurality of user vital sign data is user heart rate, perspiration rate, respiration rate, blood pressure, and body temperature, and wherein the plurality of presenter attributes are a speaker identity, a speaker voice tone, a speaker voice volume, and a speaker voice pitch;

determining a negative emotional state is experienced by the user when an attribute within the plurality of presenter attributes is present based on the plurality of analyzed user data, wherein the determined negative emotional state is selected from a group consisting of a sound volume sensitivity, a sound pitch sensitivity, a user stress level, an anxious state, a nervous state, a frightened state, a sad state, and an anger state;

receiving a plurality of calendar information associated with a plurality of user accounts of an email account, a social media account, and an instant messenger account;

identifying an upcoming web conference based on the plurality of received calendar information;

identifying an attribute within the plurality of presenter attributes is present at the identified upcoming web conference; and in response to determining the identified attribute causes the user to experience a negative emotional state, executing an audio accommodation method to modify a presenter's voice with an overlay to soften the presenter's voice for the user listening to the web conference based on the identified attribute, wherein the overlay is a voiceover that lowers a present voice volume and plays a modified presenter voice audio in a softer tone to the user.

* * * * *